US012728173B2

(12) United States Patent
Li et al.

(10) Patent No.: US 12,728,173 B2
(45) Date of Patent: Sep. 8, 2026

(54) HEPTAMETHINE CYANINE NEAR-INFRARED FLUORESCENT DYE, PREPARATION METHOD THEREFOR AND USE THEREOF

(71) Applicant: NANJING NUOYUAN MEDICAL DEVICES CO., LTD, Nanjing (CN)

(72) Inventors: Changsheng Li, Nanjing (CN); Huiming Cai, Nanjing (CN); Huidan Zhang, Nanjing (CN)

(73) Assignee: NANJING NUOYUAN MEDICAL DEVICES CO., LTD, Nanjing (CN)

( * ) Notice: Subject to any disclaimer, the term of this patent is extended or adjusted under 35 U.S.C. 154(b) by 0 days.

(21) Appl. No.: 19/327,141

(22) Filed: Sep. 12, 2025

(65) Prior Publication Data

US 2026/0007777 A1 Jan. 8, 2026

Related U.S. Application Data

(63) Continuation of application No. PCT/CN2024/105429, filed on Jul. 15, 2024.

(30) Foreign Application Priority Data

Apr. 16, 2024 (CN) ......................... 202410451606.0

(51) Int. Cl.
*A61K 49/00* (2006.01)
*A61P 35/00* (2006.01)
*C07D 209/10* (2006.01)

(52) U.S. Cl.
CPC .......... *A61K 49/0032* (2013.01); *A61P 35/00* (2018.01); *C07D 209/10* (2013.01)

(58) Field of Classification Search
CPC ..... A61K 49/00; A61K 49/0032; A61P 35/00; C07D 209/10
See application file for complete search history.

(56) References Cited

U.S. PATENT DOCUMENTS

2015/0258217 A1 9/2015 Caravan et al.

FOREIGN PATENT DOCUMENTS

| | | | |
|---|---|---|---|
| CN | 1351505 | A | 5/2002 |
| CN | 103687854 | A | 3/2014 |
| CN | 107648618 | A | 2/2018 |
| CN | 108135903 | A | 6/2018 |
| CN | 108219782 | A | 6/2018 |
| CN | 111196896 | A | 5/2020 |
| CN | 113717543 | A | 11/2021 |
| CN | 116731021 | A | 9/2023 |
| WO | 2014055253 | A1 | 4/2014 |

OTHER PUBLICATIONS

First Office Action of counterpart Chinese Patent Application No. 202410451606.0 issued on May 21, 2024.

Notice of Allowance of counterpart Chinese Patent Application No. 202410451606.0 issued on Jun. 3, 2024.

*Primary Examiner* — D. L. Jones

(57) ABSTRACT

The present disclosure provides a heptamethine cyanine near-infrared fluorescent dye, a preparation method therefor and use thereof, relating to the technical field of organic fluorescent molecules. The heptamethine cyanine near-infrared fluorescent dye has a structure as represented by following Formula I. The heptamethine cyanine near-infrared fluorescent dye provided by the present disclosure has better in vivo metabolic characteristic, no accumulation in normal tissues such as the liver, and a long time of tumor tissue developing window, is more suitable for precise diagnosis of tumors, has a certain clinical application prospect, and is applied to fluorescence development of clinical tumor and the like.

Formula I

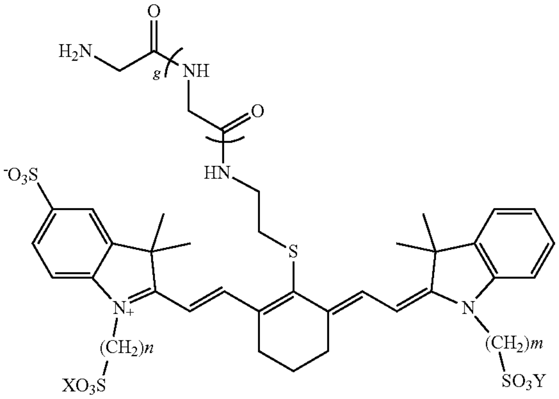

8 Claims, 4 Drawing Sheets

HEPTAMETHINE CYANINE NEAR-INFRARED FLUORESCENT DYE, PREPARATION METHOD THEREFOR AND USE THEREOF

CROSS-REFERENCE TO RELATED APPLICATIONS

The present application is a continuation application of PCT application No. PCT/CN2024/105429 filed on Jul. 15, 2024, which claims the benefit of Chinese Patent Application No. 202410451606.0 filed on Apr. 16, 2024. The contents of all of the aforementioned applications are incorporated by reference herein in their entirety.

TECHNICAL FIELD

The present disclosure relates to the technical field of organic fluorescent molecules, and particularly to a heptamethine cyanine near-infrared fluorescent dye, a preparation method therefor and use thereof.

BACKGROUND ART

Cancer seriously threatens human life and health. With the deepening of population aging and changes in people's lifestyle, challenges brought by cancers are becoming increasingly severe. Current treatment means for cancers mainly includes chemotherapy, radiotherapy, ablation, surgical resection, etc. For solid tumors, early screening, early diagnosis and early surgery can effectively improve cure rates of diseases, thereby prolonging patient survival.

With the emergence of various advanced medical devices, such as computed tomography (CT), magnetic resonance imaging (MRI), positron emission tomography (PET), near-infrared fluorescence imaging system and ultrasound (US), early detection rates of tumors are greatly improved, and important references are provided for accurate diagnosis of tumors. Compared with optical molecular imaging surgery navigation technologies such as CT and MRI, they have real-time, noninvasive, and high-resolution characteristics, and provide a brand-new imaging auxiliary means for accurate surgery of tumors. Near-infrared fluorescence imaging diagnosis has advantages in tumor diagnosis (early, mid and late), intraoperative navigation, prognosis, recurrence monitoring diagnosis and other aspects. This diagnosis method performs specific detection mainly using a near-infrared fluorescence probe (650-1,000 nm), can provide high-resolution tissue and organ images, has advantages of small biological toxicity and low spontaneous fluorescence, and helps minimize background interference.

Indocyanine green is a near-infrared fluorescent dye approved by FDA, is easy to bind to plasma proteins after intravenous injection, is metabolized into bile by the liver, and can be retained in tumor tissues through an EPR effect. It has high safety and a broad-spectrum tumor targeting effect (all solid tumors), but with relatively weak tumor targeting capability, and a clinical human dose is ≤2.0 mg/kg, thus limiting an application range thereof. Therefore, it is of great clinical significance to develop a targeting contrast imaging agent with a broad spectrum, higher fluorescence efficiency, and stronger tumor targeting capability.

CN111196896A discloses a water-soluble heptamethine cyanine near-infrared dye with a tumor targetability and use thereof. Such near-infrared dye of structural formula I, after being widely distributed in tissues throughout the body along with hemoglobin, metabolizes faster in normal tissues than in tumor tissues, and thus can be retained in the tumor tissues in a large amount, thereby playing a role in in vivo diagnosis. Tumor targeting capability verification revealed that NIR-04 exhibits stronger tumor targeting capability than ICG, with tumor retention exceeding 48 h. However, NIR-04 has a deficiency of hepatic accumulation.

Therefore, it is urgent to develop a near-infrared fluorescent dye having a strong tumor targeting capability and a long tumor imaging time.

In view of this, the present disclosure is specifically proposed.

SUMMARY

A first objective of the present disclosure lies in providing a heptamethine cyanine near-infrared fluorescent dye. The heptamethine cyanine near-infrared fluorescent dye modified by taking NIR-04 as a parent nucleus effectively solves the problem of deficiency of prolonged hepatic accumulation of NIR-04, while retaining the tumor targeting capability. That is, the heptamethine cyanine near-infrared fluorescent dye developed in the present disclosure has advantages of a strong tumor targeting capability and a long tumor imaging time.

A second objective of the present disclosure lies in providing a preparation method for a heptamethine cyanine near-infrared fluorescent dye. In the preparation method, a series of heptamethine cyanine near-infrared fluorescent dyes are prepared through further modification of NIR-04 and reactions such as amide condensation under an action of a condensing agent, deprotection of trityl protecting group with trifluoroacetic acid, nucleophilic substitution, and further deprotection.

A third objective of the present disclosure lies in providing use of the heptamethine cyanine near-infrared fluorescent dye in the preparation of a fluorescent contrast imaging agent.

A fourth objective of the present disclosure lies in providing use of the heptamethine cyanine near-infrared fluorescent dye in preparation of a tumor diagnostic drug, and use in the preparation of a diagnostic drug for liver cancer or colorectal cancer.

In order to achieve the above objectives of the present disclosure, following technical solutions are particularly adopted.

In the first aspect, the present disclosure provides a heptamethine cyanine near-infrared fluorescent dye. The heptamethine cyanine near-infrared fluorescent dye has a structure as represented by following Formula I:

Formula I

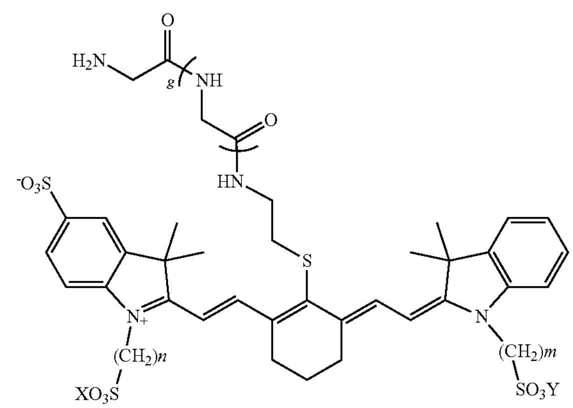;

where X or Y is each independently a hydrogen ion or a salifiable positive ion; m or n is each independently 3 or 4; and g is an integer selected from 0-20, such as 0, 1, 2, 3, 4, 5, 6, 7, 8, 9, 10, 11, 12, 13, 14, 15, 16, 17, 18, 19, and 20.

In the present disclosure, by modifying the heptamethine cyanine near-infrared fluorescent dye by taking NIR-04 as a parent nucleus, a passive targeting broad-spectrum fluorescent contrast imaging agent with good water solubility, absence of hepatic accumulation, and prolonged retention at a tumor site is obtained, and is thus applied to clinical tumor diagnosis and intraoperative navigation.

Preferably, the salifiable positive ion includes a positive alkali metal ion and/or $NH_4^+$.

Preferably, the positive alkaline metal ion is $Na^+$ and/or $K^+$.

In the second aspect, the present disclosure provides a preparation method for the heptamethine cyanine near-infrared fluorescent dye of the first aspect, where the preparation method includes following steps:

(1) mixing ((9H-fluoren-9-yl)methoxy)carbonyl triglycine, 2-(triphenylmethylthio)ethylamine, a condensing agent, a base and a reaction solvent, carrying out a condensation reaction and then performing a post-treatment, to yield intermediate a;

(2) mixing the intermediate a, trifluoroacetic acid, triisopropylsilane and water, carrying out a reaction and then performing a post-treatment, to yield intermediate b;

(3) mixing a dye molecule, the intermediate b, a base and a reaction solvent, carrying out a reaction and then performing a post-treatment to yield intermediate c, where the dye molecule has a structure as represented by following Formula II:

Formula II

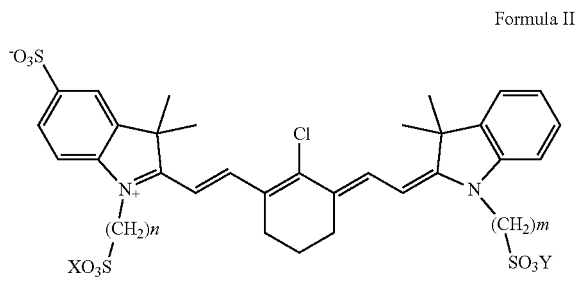

where X or Y is each independently a hydrogen ion or a salifiable positive ion; and m or n is each independently 3 or 4; and (4) mixing the intermediate c, secondary amine and a reaction solvent, carrying out a reaction and then performing a post-treatment, to yield the heptamethine cyanine near-infrared fluorescent dye.

Preferably, in step (1), a molar ratio of the ((9H-fluoren-9-yl)methoxy)carbonyl triglycine, 2-(triphenylmethylthio)ethylamine, the condensing agent and the base is 1:(0.8-1.2):(1.5-3):(2-4).

Herein, "0.8-1.2" may be, for example, 0.8, 0.9, 1, 1.1, and 1.2.

Herein, "1.5~3" may be, for example, 1.5, 1.8, 2, 2.2, 2.5, and 3.

Herein, "2~4" may be, for example, 2, 2.5, 3, 3.5, and 4.

Preferably, in step (1), a mass ratio of the reaction solvent to the ((9H-fluoren-9-yl)methoxy)carbonyl triglycine is (5-20):1, which may be, for example, 5:1, 6:1, 8:1, 10:1, 12:1, 14:1, 16:1, 18:1, and 20:1.

Preferably, in step (1), the condensing agent is any one or a combination of at least two selected from the group consisting of HATU, HBTU, HCTU, HOAT and HOBT.

Preferably, in step (1), the base is triethylamine and/or diisopropylethylamine.

Preferably, in step (1), the reaction solvent is a polar solvent.

Preferably, in step (1), the polar solvent is any one or a combination of at least two selected from the group consisting of dimethylformamide, dimethyl sulfoxide and N-methylpyrrolidone.

Preferably, in step (1), a temperature of the condensation reaction is 10° C.-40° C., which may be, for example, 10° C., 15° C., 20° C., 25° C., 30° C., 35° C., and 40° C., and a duration of the condensation reaction is 0.5 h-2 h, which may be, for example, 0.5 h, 0.6 h, 0.8 h, 1 h, 1.2 h, 1.4 h, 1.6 h, 1.8 h, and 2 h.

Preferably, in step (1), the post-treatment specifically includes following steps: adding water to a reaction solution obtained after the condensation reaction in step (1) to form a suspension; performing extraction on the suspension with an organic solvent, and collecting organic phases, followed by drying and concentration, to yield the intermediate a.

Preferably, in step (1), the organic solvent used for the extraction is ethyl acetate.

Preferably, in step (1), a volume ratio of the reaction solution, water and the organic solvent is 1:(0.8-1.2):(1-5).

Herein, "0.8-1.2" may be, for example, 0.8, 0.9, 1, 1.1, and 1.2.

Herein, "1-5" may be, for example, 1, 1.5, 2, 2.5, 3, 3.5, 4, 4.5, and 5.

Preferably, in step (2), a volume ratio of the trifluoroacetic acid, triisopropylsilane and water is (94-96):(2-3):(2-3).

Herein, "94-96" may be, for example, 94, 94.5, 95, 95.5, and 96.

Herein, "2-3" may be, for example, 2, 2.2, 2.4, 2.6, 2.8, and 3.

Preferably, in step (2), a volume ratio of a total volume of the trifluoroacetic acid, triisopropylsilane and water to the organic solvent for the extraction is 1:(0.8-1.2), which may be, for example, 1:0.8, 1:0.9, 1:1, 1:1.1, and 1:1.2.

Preferably, in step (2), a temperature of the reaction is 10° C.-40° C., which may be, for example, 10° C., 15° C., 20° C., 25° C., 30° C., 35° C., and 40° C., and a duration of the reaction is 0.5 h-2 h, which may be, for example, 0.5 h, 0.6 h, 0.8 h, 1 h, 1.2 h, 1.4 h, 1.6 h, 1.8 h, and 2 h.

Preferably, in step (2), the post-treatment specifically includes following steps: adjusting pH of a reaction solution obtained after the reaction in step (2) to be neutral, and then performing filtration, concentration and column chromatography, to yield the intermediate b.

Preferably, in step (2), an agent for adjusting the pH is a sodium carbonate solution.

Preferably, in step (3), a molar ratio of the dye molecule, the intermediate b and the base is 1:(0.8-1.2):(1.5-4).

Herein, "0.8-1.2" may be, for example, 0.8, 0.9, 1, 1.1, and 1.2.

Herein, "1.5-4" may be, for example, 1.5, 2, 2.5, 3, 3.5, and 4.

Preferably, in step (3), a mass ratio of the reaction solvent to the intermediate b is (5-20): 1, which may be, for example, 5:1, 6:1, 8:1, 10:1, 12:1, 14:1, 16:1, 18:1, and 20:1.

Preferably, in step (3), the base is triethylamine and/or diisopropylethylamine.

Preferably, in step (3), the reaction solvent is a polar solvent.

Preferably, the polar solvent is any one or a combination of at least two selected from the group consisting of dimethylformamide, dimethyl sulfoxide and N-methylpyrrolidone.

Preferably, in step (3), a temperature of the reaction is 10° C.-40° C., which may be, for example, 10° C., 15° C., 20° C., 25° C., 30° C., 35° C., and 40° C., and a duration of the reaction is 0.5 h-2 h, which may be, for example, 0.5 h, 0.6 h, 0.8 h, 1 h, 1.2 h, 1.4 h, 1.6 h, 1.8 h, and 2 h.

Preferably, in step (3), the post-treatment specifically includes following steps: adding an organic solvent to a reaction solution obtained after the reaction in step (3), followed by centrifugation and filtration, to yield the intermediate c.

Preferably, in step (3), the organic solvent is ethyl acetate and/or tert-butyl methyl ether.

Preferably, in step (4), a molar ratio of the intermediate c to secondary amine is 1:(1-2), which may be, for example, 1:1, 1:1.1, 1:1.2, 1:1.3, 1:1.4, 1:1.5, 1:1.6, 1:1.7, 1:1.8, 1:1.9, and 1:2.

Preferably, in step (4), a mass ratio of the reaction solvent to the intermediate c is (5-20):1, which may be, for example, 5:1, 6:1, 8:1, 10:1, 12:1, 14:1, 16:1, 18:1, and 20:1.

Preferably, in step (4), the secondary amine is any one or a combination of at least two selected from the group consisting of piperidine, morpholine and diethylamine.

Preferably, in step (4), the reaction solvent is a polar solvent.

Preferably, in step (4), the polar solvent is any one or a combination of at least two selected from the group consisting of dimethylformamide, dimethyl sulfoxide and N-methylpyrrolidone.

Preferably, in step (4), a temperature of the reaction is 10° C.-40° C., which may be, for example, 10° C., 15° C., 20° C., 25° C., 30° C., 35° C., and 40° C., and a duration of the reaction is 2 h-6 h, which may be, for example, 2 h, 2.5 h, 3 h, 3.5 h, 4 h, 4.5 h, 5 h, 5.5 h, and 6 h.

Preferably, in step (4), the post-treatment specifically includes following steps: adding an organic solvent to a reaction solution obtained after the reaction in step (4), and filtering to yield a crude product, and then performing liquid chromatographic purification, to yield the heptamethine cyanine near-infrared fluorescent dye.

Preferably, in step (4), the organic solvent is ethyl acetate and/or tert-butyl methyl ether.

More specifically, the heptamethine cyanine near-infrared fluorescent dye obtained in step (4) has a structure as represented by Formula I, where g is 2.

As an optional technical solution of the present disclosure, the preparation method for the heptamethine cyanine near-infrared fluorescent dye further includes following steps:

(5) mixing the heptamethine cyanine near-infrared fluorescent dye prepared in step (4), a raw material 2, a condensing agent, a base and a reaction solvent, carrying out a condensation reaction and then performing a post-treatment, to yield intermediate e, where the raw material 2 is ((9H-fluoren-9-yl)methoxy)carbonyl triglycine or (tert-butoxycarbonyl)glycylglycylglycine;

(6) performing a deprotection reaction on the intermediate e, and then performing a post-treatment, to yield the heptamethine cyanine near-infrared fluorescent dye.

More specifically, the heptamethine cyanine near-infrared fluorescent dye obtained in step (6) has a structure as represented by Formula I, where g is 5.

Preferably, in step (5), a molar ratio of the raw material 2, the heptamethine cyanine near-infrared fluorescent dye prepared in step (4), the condensing agent and the base is 1:(0.8-1.2):(1.5-3):(2-4).

Herein, "0.8-1.2" may be, for example, 0.8, 0.9, 1, 1.1, and 1.2.

Herein, "1.5-3" may be, for example, 1.5, 1.8, 2, 2.2, 2.5, and 3.

Herein, "2-4" may be, for example, 2, 2.5, 3, 3.5, and 4.

Preferably, in step (5), a mass ratio of the reaction solvent to the raw material 2 is (5-20): 1, which may be, for example, 5:1, 6:1, 8:1, 10:1, 12:1, 14:1, 16:1, 18:1, and 20:1.

Preferably, in step (5), the condensing agent is any one or a combination of at least two selected from the group consisting of HATU, HBTU, HCTU, HOAT and HOBT.

Preferably, in step (5), the base is triethylamine and/or diisopropylethylamine.

Preferably, in step (5), the reaction solvent is a polar solvent.

Preferably, in step (5), the polar solvent is any one or a combination of at least two selected from the group consisting of dimethylformamide, dimethyl sulfoxide and N-methylpyrrolidone.

Preferably, in step (5), a temperature of the condensation reaction is 10° C.-40° C., which may be, for example, 10° C., 15° C., 20° C., 25° C., 30° C., 35° C., and 40° C., and a duration of the condensation reaction is 0.5 h-2 h, which may be, for example, 0.5 h, 0.6 h, 0.8 h, 1 h, 1.2 h, 1.4 h, 1.6 h, 1.8 h, and 2 h.

Preferably, in step (5), the post-treatment specifically includes following steps: adding an organic solvent to a reaction solution obtained after the condensation reaction in step (5), and then performing filtration and drying, to yield the intermediate e.

Preferably, in step (5), the organic solvent added to the reaction solution is ethyl acetate and/or tert-butyl methyl ether.

Preferably, in step (6), the agent used for the deprotection is a secondary amine and/or trifluoroacetic acid.

Preferably, in step (6), the secondary amine used for the deprotection is any one or a combination of at least two selected from the group consisting of piperidine, morpholine and diethylamine.

Preferably, steps (5) and (6) are repeated until the heptamethine cyanine near-infrared fluorescent dye having the structure as represented by Formula I is prepared, where g is no less than 6.

In the third aspect, the present disclosure provides use of the heptamethine cyanine near-infrared fluorescent dye of the first aspect in preparation of a fluorescent contrast imaging agent.

In the fourth aspect, the present disclosure provides use of the heptamethine cyanine near-infrared fluorescent dye of the first aspect in preparation of a tumor diagnostic drug.

Preferably, the tumor is liver cancer or colorectal cancer tumor.

Compared with the prior art, the present disclosure has following beneficial effects.

(1) In the present disclosure, through further modification of NIR-04 and reactions such as amide condensation, deprotection of trityl protecting group, nucleophilic substitution, and deprotection, a heptamethine cyanine near-infrared fluorescent dye is prepared, which improves in vivo metabolic characteristic of NIR-04, and is free of deficiencies such as hepatic accumulation. The fluorescent dye is applicable to surgical navigation for tumor resection.

(2) The heptamethine cyanine near-infrared fluorescent dye prepared in the present disclosure has a broad-spectrum passive tumor targeting effect, and at the same dose, has advantages such as a stronger tumor targeting capability than that of ICG, good water solubility, long retention time in tumor, a lower dose, and absence of accumulation in normal tissues. The heptamethine cyanine near-infrared fluorescent dye not only can be applied to the preparation of fluorescent contrast imaging agents or tumor diagnostic drugs, but also has an application potential in fields such as fluorescence-guided tumor surgical resection in clinical surgery.

BRIEF DESCRIPTION OF THE DRAWINGS

In order to more clearly illustrate technical solutions in embodiments of the present disclosure or the prior art, drawings that need to be used in the description of the embodiments or the prior art will be briefly introduced below. Obviously, the drawings in the following description show some embodiments of the present disclosure, and those ordinarily skilled in the art still could obtain other drawings according to these drawings without using any inventive efforts.

DETAILED DESCRIPTION OF EMBODIMENTS

Figure 1:
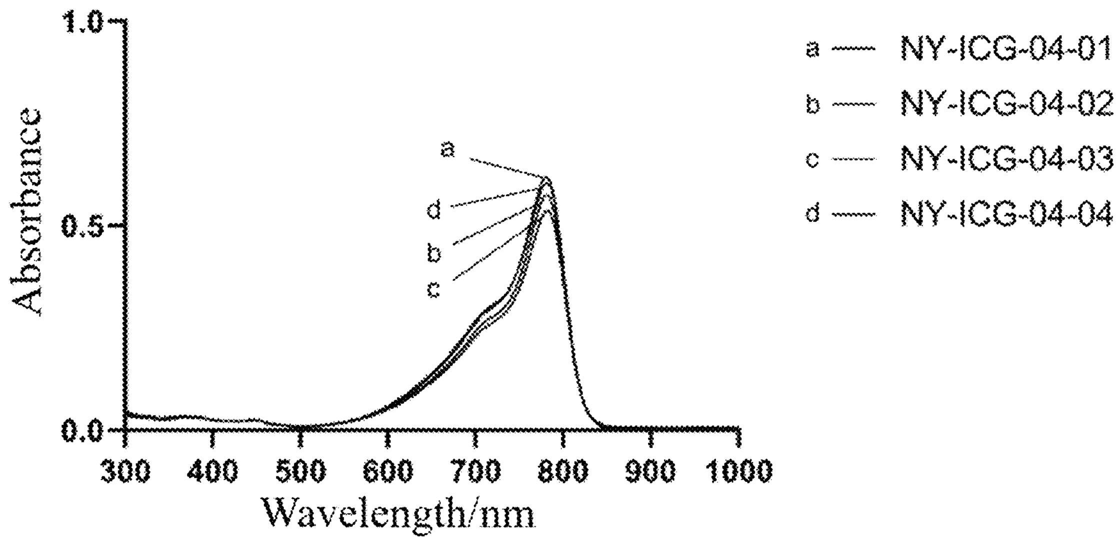
FIG. 1 is an absorption spectrum chart of NY-ICG-04-01-04 prepared by Examples 1-4.

Unless otherwise defined herein, scientific and technical terms used in connection with the present disclosure shall have the meanings that are commonly understood by those ordinarily skilled in the art. The meanings and scopes of the terms should be clear, however, in the event of any latent ambiguity, definitions provided herein take precedent over any dictionary or extrinsic definition. In the present disclosure, use of "or" means "and/or" unless otherwise stated. In addition, use of the term "include (comprise)" and other forms is non-limiting.

It should be noted that specific details are set forth in the following description in order to provide a thorough understanding of the present disclosure. However, the present disclosure can be implemented in many other modes different from those described herein. Those skilled in the art could make similar extensions without departing from the connotation of the present disclosure. Therefore, the present disclosure is not limited by embodiments disclosed below.

Technical solutions in the present disclosure will be clearly and completely described below in combination with the embodiments. Apparently, only some but not all of the embodiments are described. Based on the embodiments in the present disclosure, all of other embodiments obtained by those ordinarily skilled in the art without using any inventive efforts shall fall within the scope of protection of the present disclosure.

The present disclosure is further described below in conjunction with examples. Unless otherwise specified, materials in the examples are prepared according to existing methods, or purchased directly from the market.

Materials and sources in various following examples and comparative examples are listed below.

| Material | Manufacturer | Catalog No. |
|---|---|---|
| O-(7-Azabenzotriazol-1-yl)-N,N,N',N'-tetramethyluronium hexafluorophosphate (HATU) | Aikon | AK001LKC |
| N,N-diisopropylethylamine (DIPEA) | J&K Scientific | Cat NO: 203402 |
| ((9H-Fluoren-9-yl)methoxy)carbonyl triglycine | Bide Pharmatech | BD39294 |
| (Tert-butoxycarbonyl)glycylglycylglycine | CHIATAI TIANQING | GLS230320 |
| 2-(Triphenylmethylthio)ethylamine | Bide Pharmatech | BD00776855 |
| Triisopropylsilane ($Et_3SiH$) | Bide Pharmatech | BD155373 |
| Morpholine | Innochem | A60327 |
| Ethyl acetate | Nanjing Chemical Reagent Co., Ltd. | GB/T12589-2007 |
| Trifluoroacetic acid | Aladdin | T103291 |
| DMSO | Nanjing Chemical Reagent Co., Ltd. | HG/T 5345-2018 |
| NY-ICG-04 (NIR-04) | Self-made | — |

Example 1

The present example provides a heptamethine cyanine near-infrared fluorescent dye. The heptamethine cyanine near-infrared fluorescent dye is NY-ICG-04-01 represented by following formula:

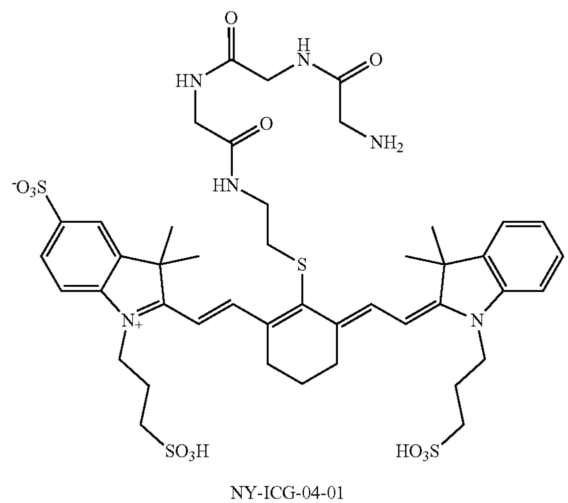

NY-ICG-04-01

A synthesis pathway of the heptamethine cyanine near-infrared fluorescent dye NY-ICG-04-01 is as follows:

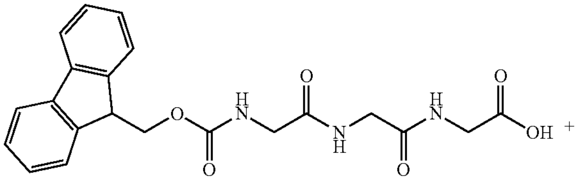

((9H-Fluoren-9-yl)methoxy)carbonyl triglycine

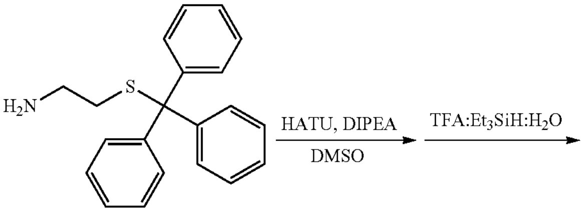

2-(Triphenylmethylthio)ethylamine

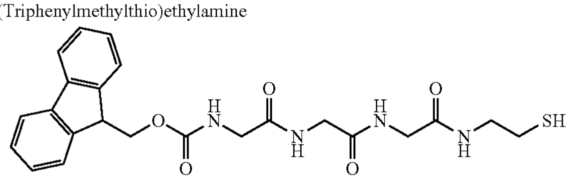

Intermediate b

Intermediate b +

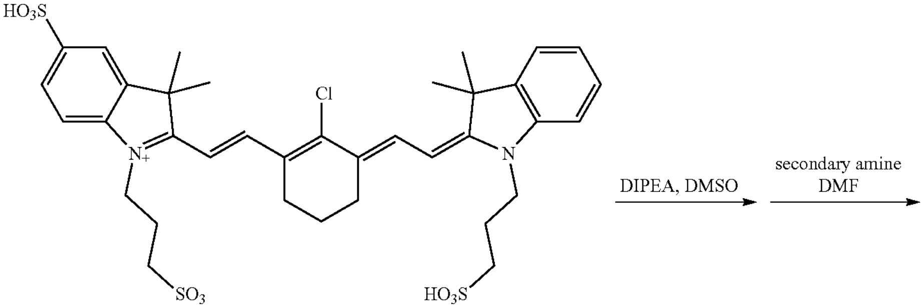

NY-ICG-04

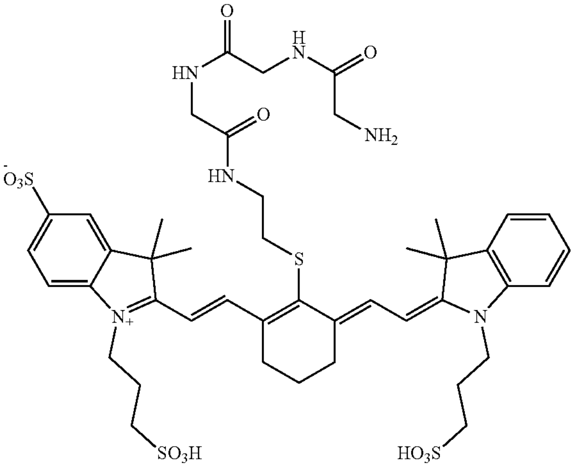

NY-ICG-04-01

A preparation method for the heptamethine cyanine near-infrared fluorescent dye NY-ICG-04-01 specifically included following steps.

(1) ((9H-Fluoren-9-yl)methoxy)carbonyl triglycine (1 g, 1.0 eq), 2-(triphenylmethylthio)ethylamine (776 mg, 1.0 eq), HATU (1.85 g, 2.0 eq), N,N-diisopropylethylamine (941 mg, 3.0 eq) and DMSO (10 mL, 10 V) were mixed and reacted at room temperature for 1 h. Reaction was monitored by TLC (DCM:MeOH=50:1). After completion of the reaction, 10 mL of water was added dropwise, mixture was extracted three times with ethyl acetate (10 mL×3), washed twice with saturated brine (20 mL×2), dried over anhydrous sodium sulfate, and then concentrated, to yield intermediate a.

(2) To the intermediate a, a mixed solution (10 mL) of trifluoroacetic acid, triisopropylsilane and water was added, where a volume ratio of trifluoroacetic acid, triisopropylsilane and water was 95:2.5:2.5. Reaction was carried out at room temperature for 1 h. After TLC monitored that the reaction was complete, pH was adjusted to be neutral with a sodium carbonate solution, a white solid was precipitated, filtered and dried, and then subjected to column chromatography, to yield intermediate b.

Structural characterization was performed by mass spectrometry and $^1$H NMR spectroscopy. Structural determination results are as follows:

LCMS (ESI): m/z: $C_{23}H_{26}N_4O_S$, $[M+H]^+$ calcd for 470.16; found, 470.8.

$^1$H NMR (600 MHz, DMSO-d6): δ 8.16 (ddt, J=17.4, 11.5, 5.8 Hz, 2H), 8.01-7.84 (m, 3H), 7.73 (dt, J=13.4, 7.4 Hz, 2H), 7.59 (t, J=6.2 Hz, 1H), 7.45-7.29 (m, 4H), 4.30 (t, J=6.6 Hz, 1H), 4.26-4.15 (m, 1H), 3.78-3.72 (m, 2H), 3.68 (t, J=6.1 Hz, 3H), 3.34 (s, 7H), 3.26-3.19 (m, 2H), 2.58-2.52 (m, 1H), 1.36-1.17 (m, 1H).

(3) NY-ICG-04 (100 mg, 1.0 eq), the intermediate b (66 mg, 1.1 eq), DIPEA (50 mg, 3.0 eq) and DMSO (1 mL, 10 V) were mixed, and reacted at room temperature for 1 h. Reaction was monitored by HPLC. When the reaction of NY-ICG-04 was indicated to be complete, reaction solution was added dropwise into ethyl acetate (10 mL), a green precipitate was precipitated, centrifuged and then allowed to settle, to yield intermediate c.

(4) To the intermediate c, DMF (1 mL) and morpholine (17 mg, 1.5 eq) were added, and reacted at room temperature for 4 h. HPLC monitored the reaction. After the reaction was indicated to be complete, reaction solution was added dropwise into ethyl acetate (10 mL), a green solid was precipitated, and subjected to preparative liquid chromatography purification to obtain a target fraction solution, followed by freeze-drying, to yield a near-infrared fluorescent probe NY-ICG-04-01.

Structural characterization was performed by mass spectrometry, $^1$H NMR spectroscopy, and $^{13}$C NMR spectroscopy. Structural determination results are as follows:

LCMS (ESI): m/z: $[M-H]^-$ $C_{44}H_{59}N_6O_{12}S_4$, calcd for 989.3; found, 989.3.

$^1$H NMR (600 MHz, DMSO-d6): δ 8.79 (d, J=14.1 Hz, 1H), 8.69 (d, J=13.9 Hz, 1H), 8.60 (t, J=5.7 Hz, 1H), 8.23 (t, J=5.9 Hz, 1H), 8.12 (t, J=5.7 Hz, 1H), 7.98 (t, J=5.9 Hz, 3H), 7.81 (d, J=1.6 Hz, 1H), 7.66-7.61 (m, 1H), 7.54 (d, J=8.0 Hz, 1H), 7.46-7.37 (m, 2H), 7.28 (t, J=7.4 Hz, 1H), 6.56 (d, J=14.3 Hz, 1H), 6.48 (d, J=14.1 Hz, 1H), 4.41-4.36 (m, 2H), 4.34-4.29 (m, 2H), 3.82 (d, J=5.7 Hz, 2H), 3.67 (d, J=5.8 Hz, 2H), 3.61 (q, J=5.9 Hz, 2H), 3.27 (q, J=6.7 Hz, 2H), 2.86 (dd, J=8.8, 6.2 Hz, 2H), 2.69 (d, J=5.3 Hz, 3H), 2.61 (t, J=6.8 Hz, 4H), 2.03 (dt, J=14.9, 7.5 Hz, 3H), 1.81 (p, J=7.0, 6.5 Hz, 2H), 1.70 (d, J=14.4 Hz, 12H).

$^{13}$C NMR (151 MHz, DMSO-d6): δ 173.06, 171.82, 169.21, 168.98, 166.74, 159.22, 158.96, 158.71, 158.45, 154.91, 146.08, 145.15, 144.68, 142.90, 142.63, 141.59, 140.75, 134.31, 133.75, 129.09, 126.58, 125.56, 122.96, 120.34, 116.47, 114.56, 112.65, 112.04, 110.49, 102.82, 101.93, 49.46, 49.01, 48.31, 43.33, 43.14, 42.33, 36.37, 27.91, 27.84, 26.35, 26.27, 23.95, 23.75, 21.13.

Example 2

The present example provides a heptamethine cyanine near-infrared fluorescent dye. The heptamethine cyanine near-infrared fluorescent dye is NY-ICG-04-02 represented by following formula:

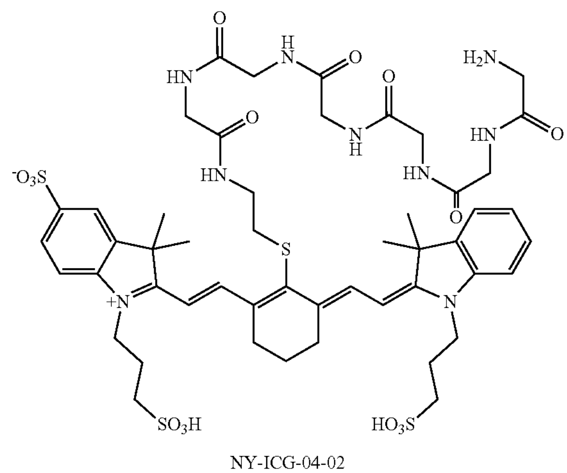

NY-ICG-04-02

A synthesis pathway of the heptamethine cyanine near-infrared fluorescent dye NY-ICG-04-02 is as follows:

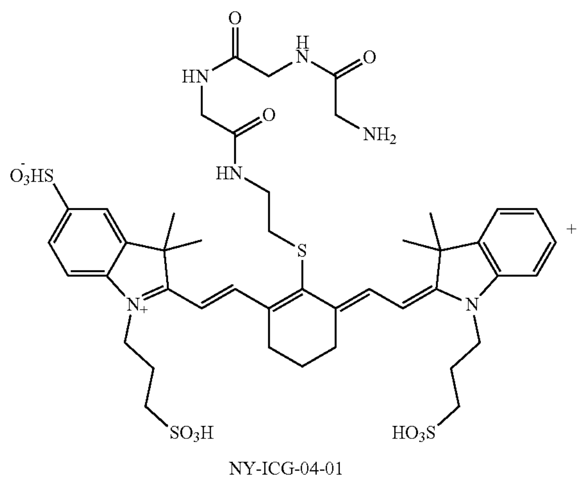

NY-ICG-04-01

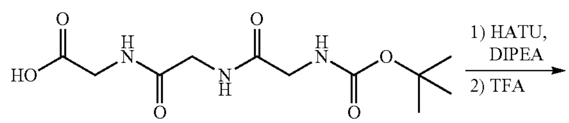

-continued

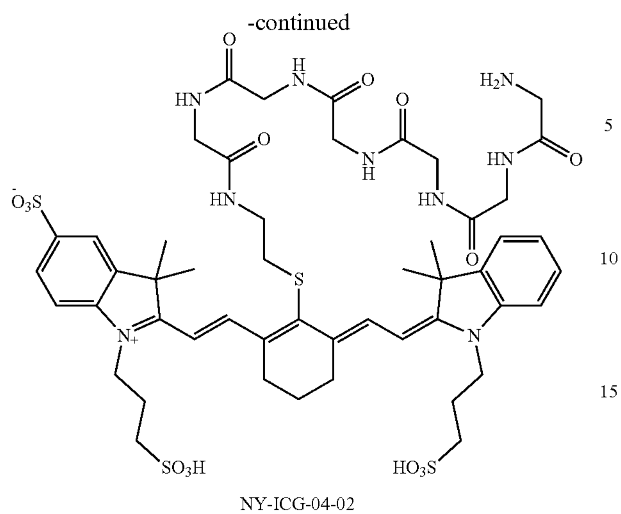

NY-ICG-04-02

A preparation method for the heptamethine cyanine near-infrared fluorescent dye NY-ICG-04-02 specifically included following steps:

(5) NY-ICG-04-01 (110 mg, 1.0 eq), BOC-glycine 3-COOH (65 mg, 2.0 eq), HATU (127 mg, 3.0 eq), DIPEA (72 mg, 5.0 eq) and DMSO (1.1 mL) were mixed and reacted at room temperature for 1 h. Reaction was monitored by HPLC. After completion of the reaction of NY-ICG-04-01, reaction solution was added dropwise into ethyl acetate (11 mL), and a green floccule substance was precipitated, filtered and dried, to yield intermediate e.

(6) To the intermediate e, TFA (100 μL) was added, and reaction was carried out at room temperature for 15 min. After TFA was removed, resultant was subjected to preparative liquid chromatography purification, to yield NY-ICG-04-02.

Structural characterization was performed by mass spectrometry, $^{1}H$ NMR spectroscopy, and $^{13}C$ NMR spectroscopy. Structural determination results are as follows:

LCMS (ESI): m/z: $[M]^+$ calcd for $C_{50}H_{68}N_9O_{15}S_4$, 1163.4; found, 1163.6.

$^{1}H$ NMR (600 MHz, DMSO-d6): δ 8.80 (d, J=14.1 Hz, 1H), 8.73-8.61 (m, 2H), 8.31 (t, J=5.9 Hz, 1H), 8.16 (t, J=5.8 Hz, 1H), 8.08 (dt, J=15.9, 5.9 Hz, 2H), 8.01 (q, J=6.3 Hz, 4H), 7.78 (s, 1H), 7.66-7.61 (m, 2H), 7.54 (d, J=8.0 Hz, 1H), 7.43 (t, J=8.3 Hz, 1H), 7.38 (d, J=8.4 Hz, 1H), 7.29 (t, J=7.4 Hz, 1H), 6.56 (d, J=14.3 Hz, 1H), 6.47 (d, J=14.0 Hz, 1H), 5.57 (s, 1H), 5.52 (s, 1H), 4.39 (t, J=7.7 Hz, 2H), 4.34-4.28 (m, 2H), 3.84 (d, J=5.7 Hz, 2H), 3.77-3.68 (m, 6H), 3.63 (q, J=6.0 Hz, 4H), 3.25 (dt, J=8.7, 5.2 Hz, 2H), 2.85 (dd, J=8.8, 6.5 Hz, 2H), 2.69 (d, J=5.3 Hz, 4H), 2.62 (td, J=6.8, 3.7 Hz, 4H), 2.04 (dq, J=14.5, 7.0 Hz, 4H), 1.81 (p, J=6.4 Hz, 2H), 1.70 (d, J=13.6 Hz, 12H).

$^{13}C$ NMR (151 MHz, DMSO-d6): δ 173.15, 171.71, 169.74, 169.54, 169.27, 166.90, 158.96, 158.70, 154.83, 146.14, 145.08, 144.58, 142.92, 142.61, 141.62, 140.69, 134.43, 133.73, 129.09, 126.58, 125.60, 122.96, 120.30, 116.49, 114.57, 112.06, 110.46, 102.89, 101.85, 49.49, 48.99, 48.29, 43.35, 43.13, 42.53, 36.15, 27.90, 27.83, 26.35, 23.94, 23.70, 21.12.

Example 3

The present example provides a heptamethine cyanine near-infrared fluorescent dye. The heptamethine cyanine near-infrared fluorescent dye is NY-ICG-04-03 represented by following formula:

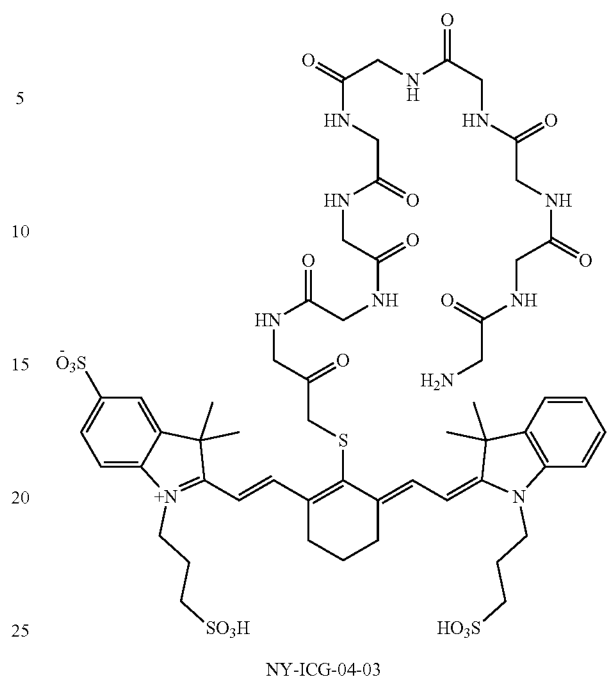

NY-ICG-04-03

With reference to Example 2, NY-ICG-04-03 was obtained upon preparation and purification.

Structural characterization was performed by mass spectrometry, $^{1}H$ NMR spectroscopy, and $^{13}C$ NMR spectroscopy. Structural determination results are as follows:

LCMS (ESI): m/z: $[M-2]^{2-}$ $C_{56}H_{77}N_{12}O_{18}S_4$, calcd for 665.2; found, 664.9.

$^{1}H$ NMR (600 MHz, DMSO-d6): δ 8.80 (d, J=14.1 Hz, 1H), 8.69 (d, J=13.8 Hz, 1H), 8.65 (t, J=5.8 Hz, 1H), 8.31 (t, J=5.8 Hz, 1H), 8.20-8.12 (m, 4H), 8.07 (dt, J=12.0, 5.8 Hz, 2H), 8.03-7.95 (m, 4H), 7.78 (s, 1H), 7.64 (td, J=8.2, 1.3 Hz, 2H), 7.54 (d, J=8.1 Hz, 1H), 7.45-7.41 (m, 1H), 7.38 (d, J=8.3 Hz, 1H), 7.29 (t, J=7.4 Hz, 1H), 6.56 (d, J=14.3 Hz, 1H), 6.46 (d, J=13.9 Hz, 1H), 5.55 (s, 1H), 5.33 (s, 1H), 4.39 (t, J=7.7 Hz, 2H), 4.30 (d, J=7.7 Hz, 2H), 3.85 (d, J=5.7 Hz, 2H), 3.78-3.68 (m, 12H), 3.64 (t, J=5.7 Hz, 4H), 3.25 (dt, J=10.5, 5.8 Hz, 2H), 2.87-2.82 (m, 2H), 2.69 (q, J=5.4 Hz, 4H), 2.63 (q, J=6.4 Hz, 4H), 2.04 (dp, J=14.7, 7.3 Hz, 4H), 1.81 (p, J=6.1 Hz, 2H), 1.70 (d, J=14.5 Hz, 12H).

$^{13}C$ NMR (151 MHz, DMSO-d6): δ 173.21, 171.67, 169.83, 169.56, 169.28, 166.92, 158.96, 158.71, 154.86, 146.19, 144.99, 144.54, 142.96, 142.60, 141.64, 140.70, 134.45, 133.71, 129.09, 126.61, 125.62, 122.97, 120.30, 116.50, 114.59, 112.07, 110.46, 102.92, 101.82, 49.50, 48.99, 48.29, 43.36, 43.12, 42.54, 42.37, 36.16, 27.89, 27.82, 26.35, 26.26, 23.93, 23.68, 21.11.

Example 4

The present example provides a heptamethine cyanine near-infrared fluorescent dye. The heptamethine cyanine near-infrared fluorescent dye is represented by following formula NY-ICG-04-04:

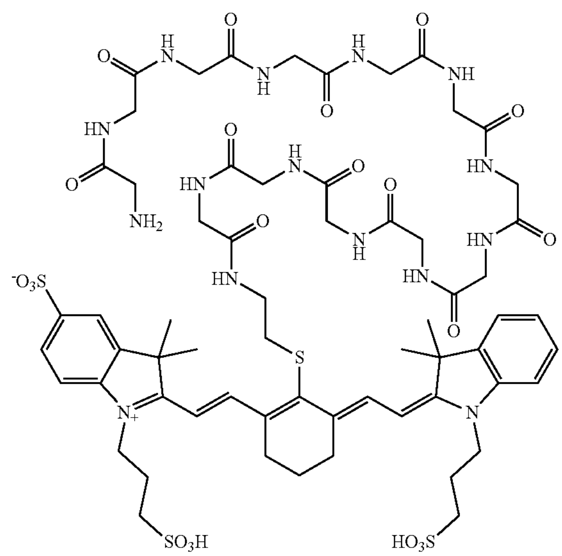

NY-ICG-04-04

With reference to Example 2, NY-ICG-04-04 was obtained upon preparation and purification.

Structural characterization was performed by mass spectrometry, $^1H$ NMR spectroscopy, and $^{13}C$ NMR spectroscopy. Structural determination results are as follows:

LCMS (ESI): m/z: $[M-2]^{2-}$ $C_{56}H_{77}N_{12}O_{18}S_4$, calcd for 750.7; found, 751.1.

$^1H$ NMR (600 MHz, DMSO-d6): δ 8.80 (d, J=14.1 Hz, 1H), 8.31 (t, J=5.6 Hz, 1H), 8.16 (dq, J=9.6, 5.3 Hz, 6H), 8.06 (dd, J=9.7, 5.6 Hz, 2H), 8.00 (d, J=14.3 Hz, 4H), 7.78 (s, 1H), 7.67-7.60 (m, 2H), 7.54 (d, J=8.0 Hz, 1H), 7.43 (t, J=7.7 Hz, 1H), 7.38 (d, J=8.3 Hz, 1H), 7.29 (t, J=7.4 Hz, 1H), 6.55 (d, J=14.2 Hz, 1H), 6.47 (d, J=14.0 Hz, 1H), 4.35 (d, J=43.6 Hz, 9H), 3.64 (t, J=6.1 Hz, 10H), 3.25 (d, J=8.1 Hz, 3H), 2.85 (t, J=7.7 Hz, 2H), 2.69 (s, 4H), 2.64-2.58 (m, 5H), 2.39 (p, J=1.9 Hz, 1H), 2.07-1.99 (m, 4H), 1.81 (s, 2H), 1.70 (d, J=15.0 Hz, 13H), 1.24 (s, 1H), 0.01 (s, 1H).

Comparative Example 1

The present comparative example provides a heptamethine cyanine near-infrared fluorescent dye. The heptamethine cyanine near-infrared fluorescent dye is NY-ICG-04 represented by following formula:

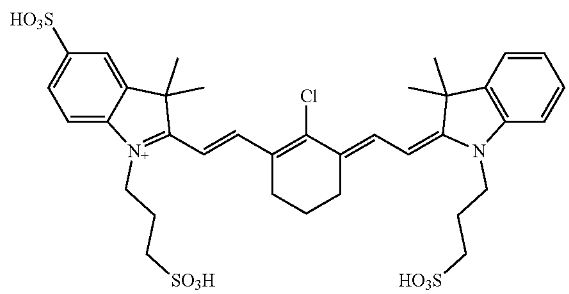

NY-ICG-04

Comparative Example 2

The present comparative example provides a heptamethine cyanine near-infrared fluorescent dye. The heptamethine cyanine near-infrared fluorescent dye is ICG represented by following formula:

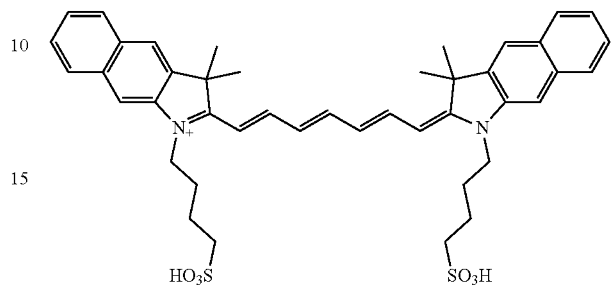

ICG

Comparative Example 3

The present comparative example provides a heptamethine cyanine near-infrared fluorescent dye. The heptamethine cyanine near-infrared fluorescent dye is YQ-04-$SCH_2CH_2CONH(CH_2CH_2O)_2CH_2CH_2NH_2$ represented by following formula (with its origin documented in Patent CN202110626918.7):

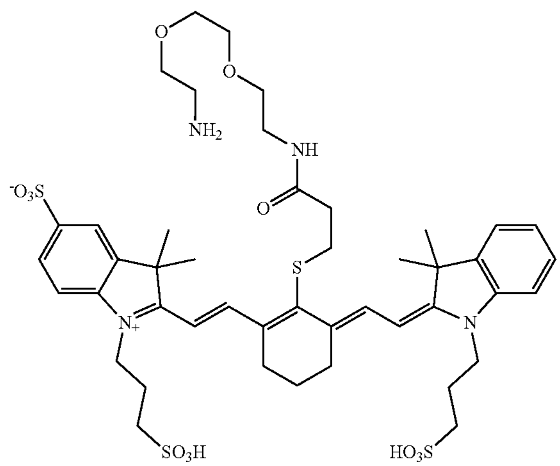

YQ-04-$SCH_2CH_2CONH(CH_2CH_2O)_2CH_2CH_2NH_2$

Test Example 1

Spectrum Test

Test samples: the heptamethine cyanine near-infrared fluorescent dyes provided by Examples 1-4.

Testing method: Various samples in the above were respectively prepared into 1 nmol aqueous solution; an absorption spectrum of each probe in a range of 500-900 nm was measured under an ultraviolet spectrophotometer (HITACHI, 3J1-0015); and a fluorescence emission spectrum of each probe in a range of 750-850 nm was measured by a microplate reader (Molecule devices, D1524R).

Test Results:

Results of absorption spectra of the above samples are shown in FIG. 1. The heptamethine cyanine near-infrared fluorescent dyes provided by Examples 1-4 had maximum absorption at about 780 nm.

Figure 2:
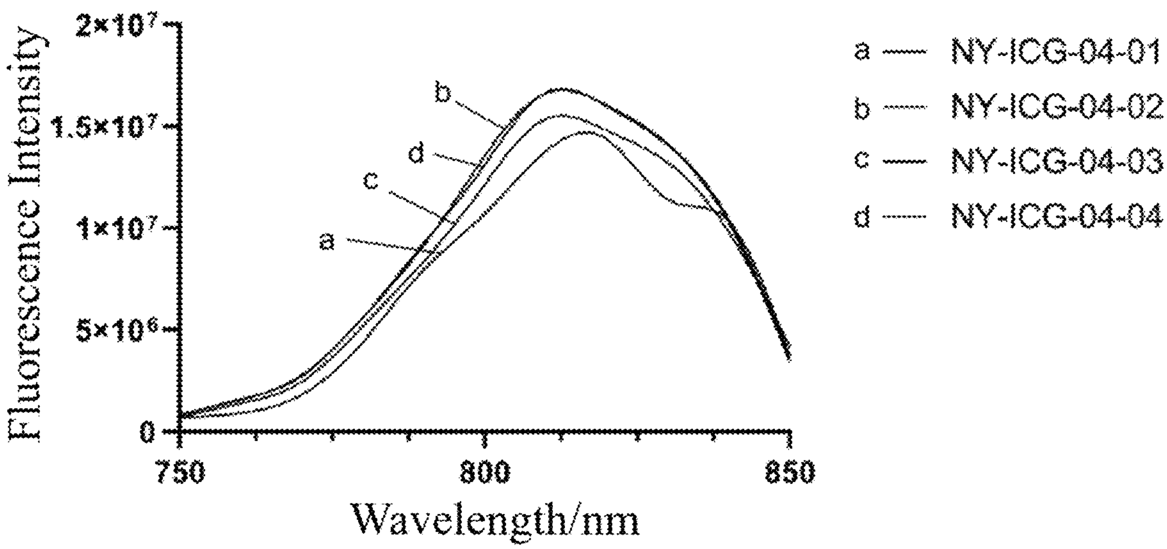
FIG. 2 is a fluorescence spectrum chart of NY-ICG-04-01-04 prepared by Examples 1-4.

Results of emission spectra of the above samples are shown in FIG. 2. The heptamethine cyanine near-infrared fluorescent dyes provided by Examples 1-4 had maximum emission spectrum at about 810 nm.

Test Example 2

In Vivo Metabolic Distribution Imaging of Normal Mice

Test samples: the heptamethine cyanine near-infrared fluorescent dyes provided by Examples 1-4, and the heptamethine cyanine near-infrared fluorescent dyes provided by Comparative Examples 1-3.

Testing method: Normal ICR mice were subjected to tail vein administration of the above samples (at a dose of 0.5 mg/kg, 100 μL of glucose injection per mouse), respectively, and the mice were dissected at 4 h, 8 h, 12 h, and 24 h, respectively. Main mouse organs (heart, liver, spleen, lung, kidney, intestine, stomach, bone, fat, etc.) were taken and subjected to fluorescence imaging by a surgical fluorescence imaging system (NANJING NUOYUAN MEDICAL DEVICES CO., LTD, 10B).

Figure 3:
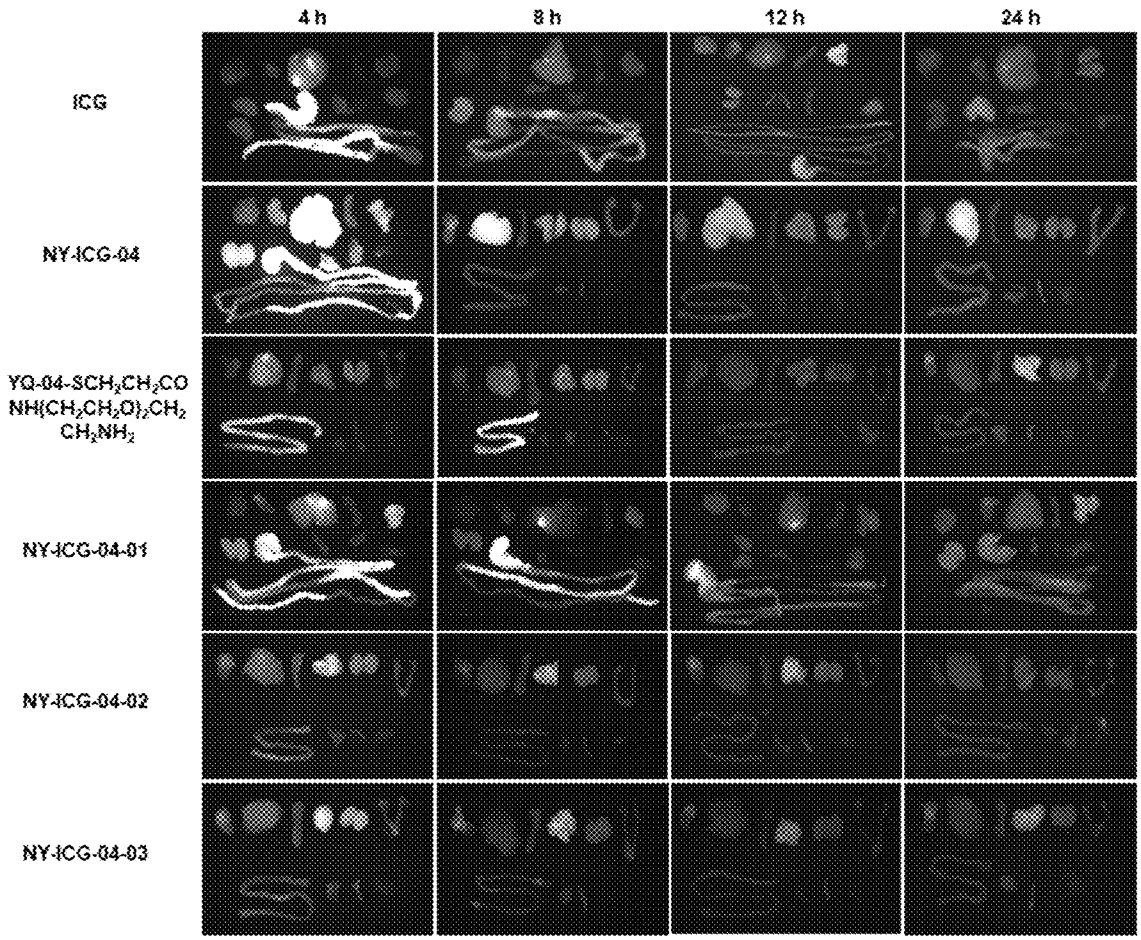
FIG. 3 shows imaging results of distribution of NY-ICG-01-03 prepared by Examples 1-3 and NY-ICG-04 provided by Comparative Example 1 in various organs of normal BCR mice.

Test Results:

Fluorescence imaging results of various samples in the above are shown in FIG. 3. In vivo metabolic conditions of the heptamethine cyanine near-infrared fluorescent dyes provided by Examples 1-3 within 24 h of administration were substantially consistent with those in Comparative Example 3, with certain pulmonary fluorescence signal, and they were substantially discharged from the liver after 8 h of administration. Compared with Comparative Example 1 (NY-ICG-04), hepatic accumulation was reduced, enabling further development and application to liver disease detection. Moreover, results demonstrate that the heptamethine cyanine near-infrared fluorescent dyes provided by various examples of the present disclosure were increased in vivo clearance with increase of quantity of amino acids introduced. Compared with Comparative Example 2 (ICG), the in vivo clearance exhibited a more pronounced increasing tendency, thus being more advantageous in practical application.

Test Example 3

Subcutaneous HepG2 Tumor-Bearing Mouse Models (Human-Derived Liver Cancer Cells) for In Vivo Imaging Test samples: the heptamethine cyanine near-infrared fluorescent dyes provided by Examples 1-4, and the heptamethine cyanine near-infrared fluorescent dyes provided by Comparative Examples 1-3.

Testing method: The subcutaneous HepG2 tumor-bearing mouse models were subjected to tail vein administration of the above samples (0.5 mg/kg, 100 μL of glucose injection), respectively. Indocyanine green (0.5 mg/kg, 100 μL of glucose injection) was taken as a control. After the administration, fluorescence imaging was performed using a surgical fluorescence imaging system (NANJING NUOYUAN MEDICAL DEVICES CO., LTD, 10B), at 0 h (before administration), 6 h, 12 h, 24 h, and 48 h in sequence.

Figure 4:
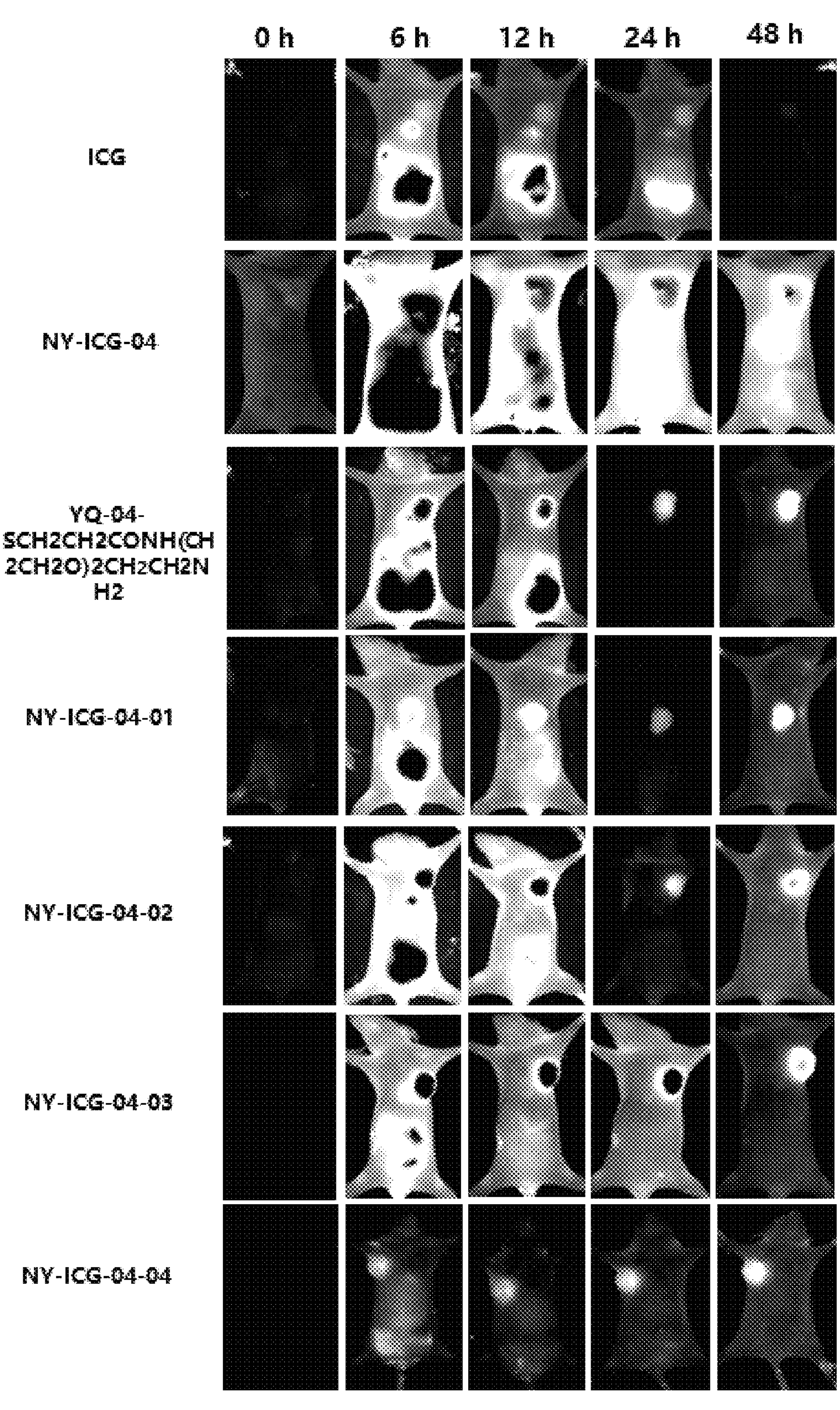
FIG. 4 shows in vivo imaging results of NY-ICG-04-01-04 prepared by Examples 1-4 and ICG provided by Comparative Example 2 in HepG2 liver cancer tumor-bearing mice.

Test Results:

Fluorescence imaging results of various samples in the above are shown in FIG. 4. Compared with Comparative Example 2 (ICG), the heptamethine cyanine near-infrared fluorescent dyes provided by the examples of the present disclosure had a stronger tumor targeting capability in liver cancer and a longer tumor developing time.

Compared with Comparative Example 1 (NY-ICG-04), the compounds had a substantially constant tumor targeting capability, and could effectively address the deficiency of hepatic accumulation and non-metabolism in Comparative Example 1.

Compared with Comparative Example 3 (YQ-04-$SCH_2CH_2CONH(CH_2CH_2O)_2CH_2CH_2NH_2$), the compounds of the present disclosure had a comparable or stronger tumor targeting capability, a rapid discharge rate in normal tissues, a rapid decline of background signal in normal tissues, and potential tumor detecting capability and clinical application prospect.

Test Example 4

Test sample: the heptamethine cyanine near-infrared fluorescent dye provided by Example 3.

Testing method: colorectal cancer (HCT116) tumor-bearing mouse models were subjected to tail vein administration of probe NY-ICG-04-03 (0.5 mg/kg, 100 μL of glucose injection). After the administration, fluorescence imaging was performed by a surgical fluorescence imaging system (NANJING NUOYUAN MEDICAL DEVICES CO., LTD, 10B), at 0 h (before administration), 6 h, 12 h, 24 h, and 48 h in sequence.

Figure 5:
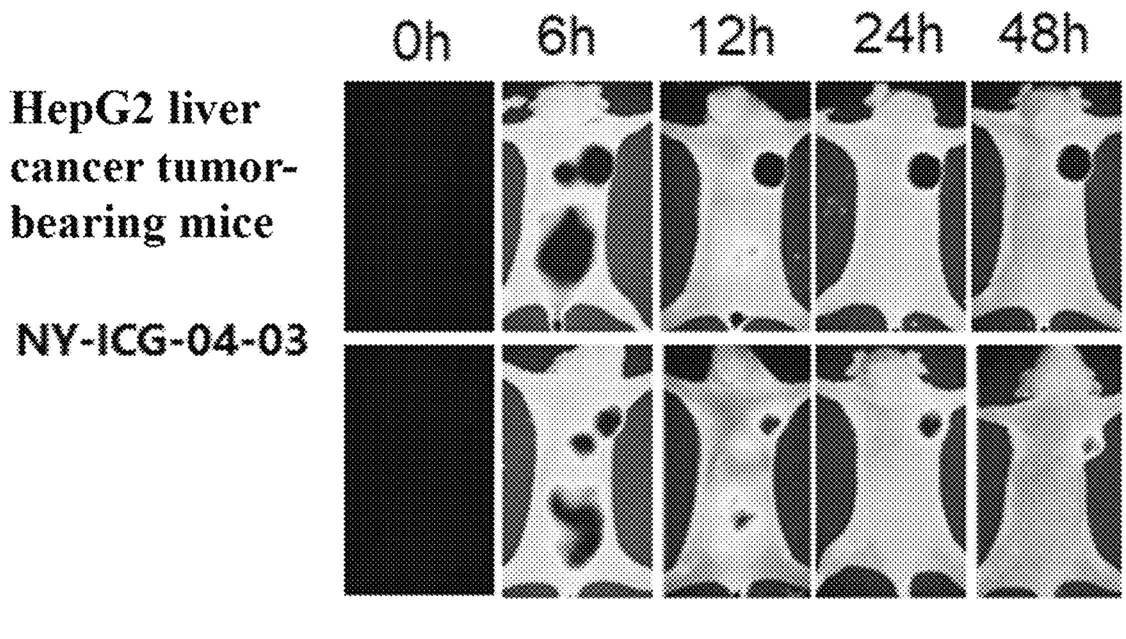
FIG. 5 shows in vivo imaging results of NY-ICG-04-03 prepared by Example 3 in HCT116 colorectal cancer tumor-bearing mice.

Test Results:

Fluorescence imaging results of the above probe NY-ICG-04-03 is shown in FIG. 5. The probe NY-ICG-04-03 likewise had a good tumor targeting capability in the colorectal cancer (HCT116) tumor-bearing mice, had a potential clinical application prospect, and demanded further research and development in order to apply it to clinical surgery.

Finally, it should be noted that various examples in the above are merely used for illustrating the technical solutions of the present disclosure, rather than limiting the present disclosure; while the detailed description is made to the present disclosure with reference to the preceding examples, those ordinarily skilled in the art should understand that they still could modify the technical solutions described in various preceding examples, or make equivalent substitutions to some or all of the technical features therein; these modifications or substitutions do not make corresponding technical solutions essentially depart from the scope of the technical solutions of various examples of the present disclosure.

The invention claimed is:

1. A heptamethine cyanine near-infrared fluorescent dye, wherein the heptamethine cyanine near-infrared fluorescent dye has a structure as represented by following Formula I:

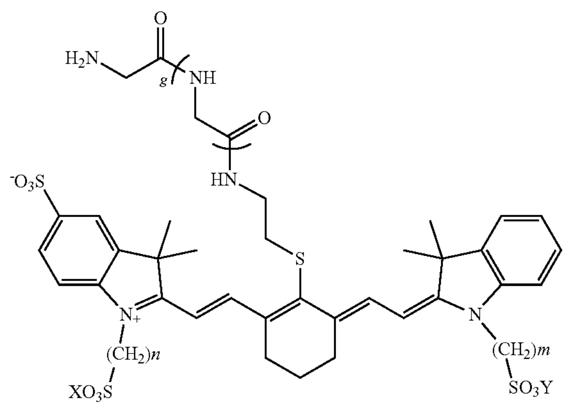

Formula I;

wherein X and Y are each independently a hydrogen ion or a salifiable positive ion; m and n are each independently 3 or 4; g is an integer selected from 0-20; and the salifiable positive ion comprises a positive alkali metal ion and/or $NH_4^+$.

2. The heptamethine cyanine near-infrared fluorescent dye according to claim 1, wherein the positive alkaline metal ion is $Na^+$ and/or $K^+$.

3. A preparation method for the heptamethine cyanine near-infrared fluorescent dye according to claim 1, comprising following steps:

(1) mixing ((9H-fluoren-9-yl)methoxy)carbonyl triglycine, 2-(triphenylmethylthio)ethylamine, a condensing agent, a base and a reaction solvent, carrying out a condensation reaction, adding water to a reaction solution obtained after the condensation reaction in step (1) to form a suspension, performing extraction on the suspension with an organic solvent, and collecting organic phases, followed by drying and concentration to yield intermediate a;

(2) reacting the intermediate a with trifluoroacetic acid and triisopropylsilane in water, adjusting pH of a reaction solution obtained after the reaction in step (2) to be neutral, and then performing filtration, concentration and column chromatography to yield intermediate b;

(3) reacting a dye molecule having has a structure as represented by following Formula II with the intermediate b and a base in a reaction solvent, adding an organic solvent to a reaction solution obtained after the reaction in step (3), followed by centrifugation and filtration to yield intermediate c, Formula II

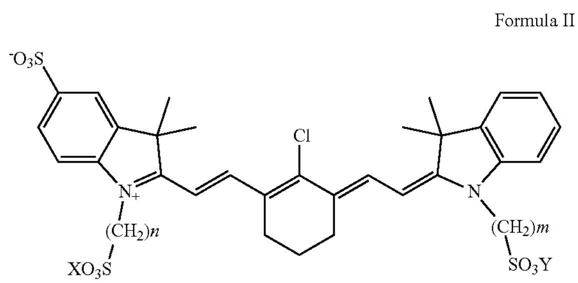

wherein X and Y are each independently a hydrogen ion or a salifiable positive ion; and m and n are each independently 3 or 4; the salifiable positive ion comprises a positive alkali metal ion and/or $NH_4^+$; and (4) reacting the intermediate c with secondary amine in a reaction solvent, adding an organic solvent to a reaction solution obtained after the reaction in step (4), and filtering to yield a crude product, and then performing liquid chromatographic purification to yield the heptamethine cyanine near-infrared fluorescent dye.

4. The preparation method for the heptamethine cyanine near-infrared fluorescent dye according to claim 3, wherein in step (1), a molar ratio of the ((9H-fluoren-9-yl)methoxy) carbonyl triglycine, the 2-(triphenylmethylthio)ethylamine, the condensing agent and the base is 1:(0.8-1.2):(1.5-3):(2-4); and/or in step (1), a mass ratio of the reaction solvent to the ((9H-fluoren-9-yl)methoxy)carbonyl triglycine is (5-20):1; and/or in step (1), a temperature of the condensation reaction is 10° C.-40° C., and a duration of the condensation reaction is 0.5 h-2 h.

5. The preparation method for the heptamethine cyanine near-infrared fluorescent dye according to claim 3, wherein in step (2), a volume ratio of the trifluoroacetic acid, the triisopropylsilane and the water is (94-96):(2-3):(2-3); and/or in step (2), a temperature of the reaction is 10° C.-40° C., and a duration of the reaction is 0.5 h-2 h.

6. The preparation method for the heptamethine cyanine near-infrared fluorescent dye according to claim 3, wherein in step (3), a molar ratio of the dye molecule, the intermediate b and the base is 1:(0.8-1.2):(1.5-4); and/or in step (3), a mass ratio of the reaction solvent to the intermediate b is (5-20):1; and/or in step (3), a temperature of the reaction is 10° C.-40° C., and a duration of the reaction is 0.5 h-2 h; and/or in step (3), the organic solvent is ethyl acetate and/or tert-butyl methyl ether.

7. The preparation method for the heptamethine cyanine near-infrared fluorescent dye according to claim 6, wherein in step (4), a molar ratio of the intermediate c to the secondary amine is 1:(1-2); and/or in step (4), a mass ratio of the reaction solvent to the intermediate c is (5-20):1; and/or in step (4), a temperature of the reaction is 10° C.-40° C., and a duration of the reaction is 2 h-6 h; and/or in step (4), the organic solvent is ethyl acetate and/or tert-butyl methyl ether; and/or the heptamethine cyanine near-infrared fluorescent dye obtained in step (4) has a structure as represented by Formula I, wherein g is 2.

8. The preparation method for the heptamethine cyanine near-infrared fluorescent dye according to claim 7, wherein the preparation method for the heptamethine cyanine near-infrared fluorescent dye further comprises following steps:

(5) mixing the heptamethine cyanine near-infrared fluorescent dye prepared in step (4), a raw material 2, a condensing agent, a base and a reaction solvent, carrying out a condensation reaction, adding an organic solvent to a reaction solution obtained after the condensation reaction in step (5), and then performing filtration and drying, to yield intermediate e, where the raw material 2 is ((9H-fluoren-9-yl)methoxy)carbonyl triglycine or (tert-butoxycarbonyl)glycylglycylglycine; and (6) performing a deprotection reaction on the intermediate e, and then performing separation, to yield the heptamethine cyanine near-infrared fluorescent dye, wherein the heptamethine cyanine near-infrared fluorescent dye obtained in step (6) has a structure as represented by Formula I, wherein g is 5; and/or steps (5) and (6) are repeated until the heptamethine cyanine near-infrared fluorescent dye having the structure as represented by Formula I is prepared, wherein g is no less than 6.

* * * * *